(12) United States Patent
Sluka et al.

(10) Patent No.: US 7,517,700 B2
(45) Date of Patent: Apr. 14, 2009

(54) CORE-SHELL PARTICLES

(75) Inventors: Peter Sluka, Weilheim (DE); Sebastian Heimerl, Tutzing (DE); Konrad Kuerzinger, Penzberg (DE); Thomas Fischer, Rauenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/774,034

(22) Filed: Jul. 6, 2007

(65) Prior Publication Data

US 2008/0032421 A1 Feb. 7, 2008

Related U.S. Application Data

(62) Division of application No. 10/297,238, filed on Aug. 11, 2003, now Pat. No. 7,256,054.

(51) Int. Cl.
*G01N 33/553* (2006.01)
(52) U.S. Cl. ............... 436/525; 427/2.13; 436/524; 436/529
(58) Field of Classification Search ............... None
See application file for complete search history.

(56) References Cited

U.S. PATENT DOCUMENTS

| 5,248,772 A |   | 9/1993 | Siiman et al. ............ 536/112 |
| 5,445,970 A | * | 8/1995 | Rohr ...................... 436/526 |
| 5,552,086 A |   | 9/1996 | Siiman et al. ........... 252/408.1 |
| 5,945,293 A |   | 8/1999 | Siiman et al. ............ 435/7.24 |

FOREIGN PATENT DOCUMENTS

| EP | 0369515 B1 | 5/1990 |
| EP | 0489465 B1 | 6/1992 |

OTHER PUBLICATIONS

Beesley, J.E. et al., "A New Perspective for Cytochemical Marking," Microscopy Handbooks (1989) 1-14.
Behnke, Olay, "Non-specific binding of protein-stabilized gold sols as a source of error in immunocytochemistry," European Journal of Cell Biology, 41, 326-338 (1986).
De Mey, J., "The Prepartaion and Use of Gold Probes," Immunocytochemistry, (1986) 115-145.
Frens, G., "Controlled Nucleation for the Regulation of the Particle Size in Monodisperse Gold Suspensions," Nature Physical Science, vol. 241, Jan. 1, 1973.
Hermanson, G.T., "Preparation of Colloidal-Gold Labeled Proteins," Bioconjugates 593-604.
Meisel, D. et al., "Catalysis of Methyl Viologen Radical Reactions by Polymer-Stabilized Gold Sols," J. Phys. Chem., 1981, 85, 179-185.
Pawlowski, Andrzej et al., "A new method of non-cross-linking conjugation of polysaccharides to proteins via thioetherbonds for the preparation of saccharide protein conjugate vaccines," Vaccine 17 (1999) 1474-1483.

* cited by examiner

*Primary Examiner*—Christopher L Chin
(74) *Attorney, Agent, or Firm*—Marilyn Amick; Roche Diagnostics Operations, Inc.

(57) ABSTRACT

Colloidal metal particles having a coating comprising non cross-linked, SH-activated dextran or aminodextran. Biomolecules may be linked directly or indirectly to the particles, which are useful as detection reagents in immunological assays.

3 Claims, 3 Drawing Sheets

CORE-SHELL PARTICLES

RELATED APPLICATIONS

This application is a divisional of Ser. No. 10/297,238 filed Aug. 11, 2003 now U.S. Pat. No. 7,256,054 claiming priority to PCT/EP01/06404 filed Jun. 6, 2001 and DE 10027776.4 filed Jun. 7, 2000.

FIELD OF THE INVENTION

The present invention concerns colloidal metal particles coated with non cross-linked sulfhydryl (SH)-activated dextran or aminodextran as well as the production and use of such particles in immunological test methods.

BACKGROUND OF THE INVENTION

In recent years colloidal metal particles have been extensively used in biological, biochemical and immunological investigations. Especially in the field of immunological assays, the application of colloidal metal particles for labeling of any type of biomolecule has been very successful.

For the production of colloidal metal particles, in particular colloidal gold particles, many different methods have been described. Colloidal gold particles are usually obtained by the reduction of solutions of tetrachloroauric acid, and relevant biomolecules are bound to these particles by adsorption in one or several further steps. The size of the colloidal metal particles can be controlled specifically by means of the initial concentration of the different reaction partners (G. Frens, *Nature Physical Science* 241:20-22, 1973). Variation of particle size can also be optimized by specific selection of the production procedure as described in EP B 426,300.

The binding of biomolecules such as, for example, antibodies, lectins or even nucleic acids, is mainly adsorptive, with the respective loading conditions strongly depending on the physico-chemical properties, e.g., isoelectric point, of the biomolecule. Principal reflections on the coating of colloidal metal particles can be found in the relevant technical literature, e.g., deMey, "The Preparation and Use of Gold Probes," in Immunocytochemistry, J. M. Polak and S. V. Noorden, pp. 115-145, Wright, Bristol, 1986 and G. T. Hermanson, "Preparation of Colloidal-Gold-Labeled Proteins," in Bioconjugate Techniques, pp. 593-604. Academic Press, 1996.

It has been proven to be necessary and useful to stabilize colloidal metal particles coated with biomolecules by adding further appropriate substances. The addition of such stabilizing and blocking substances produces the effect that probably non-saturated, "sticky" sites on the particles are blocked. In addition, by these substances the aggregation of the particles is minimized, and the re-diffusion of the relevant biomolecule is reduced.

State of the art stabilizers are, among others, inert proteins such as, for example, bovine serum albumin or water-soluble technical polymers such as polyethylene glycol (molecular weight of 20,000 Da), polyvinyl pyrrolidone, polyvinyl alcohol, polyvinyl sulfate, dextran as well as gelatin, cf., e.g., De Mey, supra; Beesly, J. E., "Colloidal Gold: A New Perspective for Cytochemical Marking," Microscopy Handbooks 17, Oxford University Press, 1989, in particular pp. 1-14; Behnke, *Eur. J. Cell. Biol.* 41: 326-338, 1986; DE 2420531 C3; and Meisel et al., *J. Phys. Chem.* 85:179-187, 1981.

The direct coating of biomolecules on the surface of colloidal metal particles has, however, also some important disadvantages. Such a disadvantage is, for example, that successful methods cannot be transferred easily from one biomolecule to a second, and that the stability of such particles has proven to be problematic (cf. de Mey, supra, p. 116 and pp. 122-123).

To avoid such problems of the older state of the art, some new methods have been developed in recent years. In particular the so-called core-shell particles are to be mentioned here. Core-shell particles consist of a (usually) metal core and of a shell surrounding the particle completely. Important examples of such shell substances are, for example, bovine serum albumin (BSA), described in EP 258,963 and EP 428,412, denatured proteins such as, for example, gelatin, water-soluble polymers such as, e.g., aminodextran (U.S. Pat. No. 5,248,772) and shells made of low-molecular thiol compounds or thiolized proteins (EP 489 465).

To stabilize the shell, the shell substances are usually cross-linked, e.g., U.S. Pat. No. 5,248,772. Such shells contain functional groups to which the desired biomolecules can bind in a covalent way as it is generally known.

The covalent coupling of the biomolecules to the core-shell particles has some advantages over the direct adsorptive binding to the colloidal surface. By covalent coupling, bleeding of the biomolecules can be avoided. Furthermore, unspecific interactions are stopped which are provoked by the remaining free surface areas inaccessible for adsorption during the adsorptive loading procedure. A post-treatment of the surface by adding stabilizers is not necessary with core-shell particles. By the use of a well-soluble hydrophilic shell, the stability of the resulting core-shell-protein conjugates can be remarkably improved. Instability caused by the aggregation of the conjugates, as it is repeatedly observed, with adsorptively loaded colloidal-protein conjugates can thus be avoided. Furthermore, covalent coupling of the proteins to the core-shell particles is to a large extent independent of the physico-chemical properties of the proteins, so that even proteins can be used which are not suitable for an adsorptive binding.

The shell substances used in the state of the art adsorb to the metal surface by complex and hitherto not completely understood mechanisms involving electrostatic as well as hydrophobic interactions. The type of shell substance determines which bond type prevails when the shell substances bind to the colloidal metal particles.

Interactions of metals, in particular gold, with compounds containing sulfur lead to a reinforced adsorptive binding. EP 369,515 describes the coating of colloidal gold particles with low-molecular compounds containing thiol. By additional functional groups, the relevant biomolecules can be bound to this thiol shell.

It is also known from the state of the art that chemically cross-linked aminodextrans can be used as the shell substance (U.S. Pat. No. 5,248,772). Cross-linking of aminodextran is required to give sufficient stability to the particles produced in such a way. A further disadvantage of the method described in U.S. Pat. No. 5,248,772 is that SH groups suitable for coupling must be inserted into the shell of cross-linked aminodextran afterwards. Such a procedure requires several additional working steps. In addition, the insertion rate of the SH groups can only be controlled less exactly, and the analysis of the insertion efficiency is almost not possible.

SUMMARY OF THE INVENTION

In the state of the art, no core-shell particles based on aminodextran are known which can be produced easily, quickly and without high costs and which do not need any further treatment steps such as, for instance, the cross-linking of the aminodextran shell or a subsequent insertion of functional groups, e.g., for coupling chemistry on SH basis.

It was therefore an object to provide improved core-shell particles avoiding as much as possible the disadvantages of the state of the art.

This object is achieved by the invention defined in more detail in the claims.

The present invention provides colloidal metal particles with an SH-dextran or SH-aminodextran shell which can be produced easily and reproducibly and which have many advantages when used, especially in immunoassays. The invention concerns in particular colloidal metal particles with a shell surrounding the metal particles (core-shell metal particles) wherein the shell comprises non cross-linked dextran or aminodextran carrying SH groups.

DETAILED DESCRIPTION OF THE INVENTION

Figure 1:
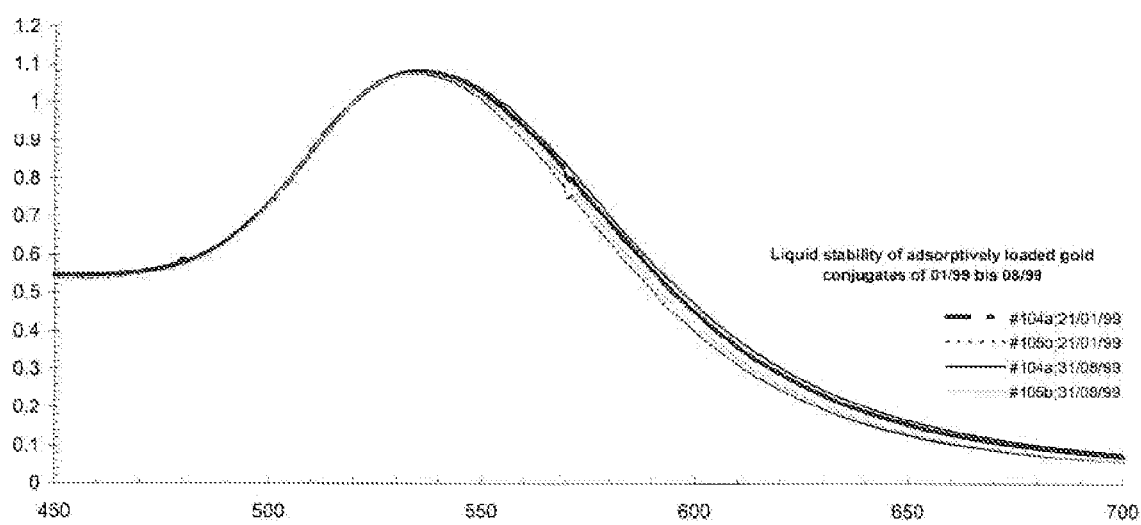
FIG. 1: UV/Vis analysis of antibody gold conjugates produced according to the state of the art Under the storage conditions chosen (approximately 7 months at 4° C.), the UV/Vis analysis shows that the curves of both conjugate batches include a remarkable change in the curve form before and after stress. This means that the conjugates tested have been strongly changed by their storage at 4° C. for approximately 7 months. In other words, these conjugates are not stable under the conditions tested.

The terms "colloidal core-shell particles" and "colloidal metal particles with a shell" are applied in the following to describe particles with a metal core and a shell/coating consisting of one or several non-metal components.

As metal core particles, all colloidal metal particles producible according to method of the state of the art can be considered. Preferably, the metals concerned are noble metals, in particular gold or silver and particularly preferably gold.

Dextrans belong to a polysaccharide group known to the expert. Preferably, molecules with molecular weights from 5,000 to 2,000,000 Da, also preferable from 20,000 to 1,000,000 Da and particularly preferable from 30,000 to 100,000 Da are used.

Into commercially available dextrans or aminodextrans, SH groups are inserted; aminodextrans are here particularly preferred. The insertion of SH groups is a chemical reaction of, for instance, activated carboxylic acids with the amino groups. For this, reagents of the type S-acetyl-thiopropionyl-acid-N-hydroxysuccinimide ester (SATP), N-succinimidyl-S-acetylthioacetate (SATA) and S-acetyl-mercapto-succinic anhydride (SAMBA) are preferable used. Activation of the OH groups of the dextrans is, for example, initiated by 1-cyano-4-(dimethylamino)-pyridinium tetrafluoroborate (CDAP) and the insertion of SH groups by subsequent adding of SH-protected aminothiols, e.g., S-acetyl cysteamine.

When using SATP for the insertion of SH groups in aminodextran, by far the biggest part of the amino groups should be converted. The SH groups are then released by adding hydroxylamine. Particularly advantageous are SH-aminodextran with amino groups converted to an extent of at least 70%, particulary preferably 80% and very particularly preferable 90%, and which carry an SH functionality.

Activation of aminodextran by means of SATP can be carried out under very variable conditions with preferred pH values of 7.5 to 9.0 and temperatures of 4° C. or room temperature and periods from 2 to 24 hours. It has been proven to be particularly suitable to work with a pH of 8.5 at room temperature and to fix a reaction period of approximately 3 hours. The release of the SH groups, for example, by adding hydroxylamine is particularly preferable under weakly acid pH conditions, particularly preferable with a pH of 6.0 to 6.5.

If in the following SH-aminodextran or aminodextran with active SH groups or SH-activated aminodextran is mentioned, this generally includes SH-aminodextrans or SH-dextrans as they may, for example, be produced according to the methods discussed above.

In the relevant state of the art (EP 489,465), it is explicitly mentioned that for post-coating, stabilization and provision of reactive groups, short-chain molecules, e.g., alkylthiols with a maximum chain length of 24 C atoms, should be used. There are good reasons why the upper chain length limit is set to 24 C atoms in EP 489,465. The reason for this fear of long-chain molecules with more that 2 or 3 SH groups is evident. The expert must assume that long-chain molecules such as, for example, SH-aminodextrans, do not stabilize metal sol particles but lead to agglutination.

Precisely, these agglomerates or nuggets of may colloidal metal particles constitute the biggest problem in the field of technology and lead to instabilities and problems caused by unspecific binding.

Surprisingly, it has however been shown that SH-aminodextrans are very advantageous when used for post-coating and stabilization of colloidal metal particles. This post-treatment leads to remarkably stable particles so that cross-linking of the aminodextran monomers as it is usually carried out (U.S. Pat. No. 5,248,772) is no longer necessary at all. Obviously, the binding to the metal surface by means of the SH functionalities is so stable that neither an additional post-coating for saturation of free "sticky" surface components nor a cross-linking of the SH-aminodextran molecules is required to avoid re-diffusion (bleeding of unstable molecule bindings). A subject matter of the invention is therefore the use of SH-aminodextran for coating and stabilization of colloidal metal particles.

The invention relates to a method for the production of colloidal metal particles with an SH-aminodextran shell wherein the colloidal metal particles and the SH-activated aminodextran are incubated under suitable conditions. Surprisingly, the core-shell particles according to the invention are easy to prepare. Simple mixing of the colloidal gold solution and the solution of the SH-modified aminodextran under a controlled pH at room temperature provokes the forming of the core-shell particles according to the invention.

The thus resulting particles are only washed and can be used for coupling to linker or biomolecules without the occurrence of stabilization via cross-linking.

The coating of the gold sol produced according to the standard procedure with SH-aminodextran is preferably performed in the range from pH 5.0 to 7.0, particularly preferably between pH 5.5 and pH 6.5. The reaction temperature and reaction period can be broadly varied, but 4° C. or room temperature for 2 to 24 hours is preferred.

The invention especially relates to colloidal particles with a shell surrounding these metal particles (core-shell metal particles) wherein the shell comprises non cross-linked aminodextran carrying SH groups.

Particularly preferably, these colloidal metal particles according to the invention consist of noble metals, in particular of gold and silver, very particularly preferably of gold.

Not all SH groups are blocked by the coating and interaction with the metal surface. Many SH groups are surprisingly not involved in the interaction with the metal surface. These SH groups which are still accessible after their coating represent an optimum binding site for further molecules, in particular biomolecules.

Thus it has been proven to be very advantageous to use SH-reactive homo- or hetero-bifunctional linkers which, on the one hand, provoke a covalent binding to the SH group of the SH-aminodextran and, on the other hand, also bind covalently to the biomolecule wanted via a specifically chosen functionality. Preferred functionalities on the biomolecules to be coupled are, for example, $NH_2$ or SH groups.

Moreover the invention concerns a method for the production of conjugates consisting of biomolecules, in particular antibodies, and colloidal SH-aminodextran metal particles.

The loading of the particles with the biomolecules is carried out under appropriate buffer conditions. Particularly preferably at a pH ranging from 6.5 to 7.0, biomolecules activated by maleimide can be coupled via covalent binding to the gold particles loaded with SH-aminodextran. The coupling of the biomolecules is preferably performed overnight, i.e., over a period of approximately 10 to 30 hours at a temperature that is not critical and can be about 4° C. or room temperature. For blocking of the still present reactive maleimide groups, reagents such as thioglucose or cysteine are used. SH groups are blocked by adding reagents such as indo-acetamide, N-methylmaleimide (NMM) or N-ethylmaleimide (NEM).

As biomolecules, all molecules used in the usual diagnostic test methods are considered. According to the invention these are preferably nucleic acids, peptides and proteins. Other biomolecules such as, for example, haptens, lipids and polysaccharides, also have a beneficial effect when used.

Particularly preferred are biomolecules from the group of proteins, in particular proteins representing good binding partners for further biomolecules, and very particularly preferred are lectins, avidin, streptavidin and antibodies.

According to the invention, the term "antibody" also includes, besides the intact immunoglobin, all antibody fragments. These are, for example, Fab, Fab' and F(ab')$_2$ fragments. The term "antibody" without the modifier "monoclonal" or "polyclonal" always includes both types of antibodies as well as chimeric constructs and all fragments mentioned above.

The present invention therefore concerns, in another form, core-shell particles with a coating of non cross-linked SH-aminodextrans to which further molecules are bound via the SH group of the SH-aminodextran.

For this covalent binding or coupling of biomolecules, it is advantageous to use SH-reactive linker molecules, i.e., molecules with at least two groups suitable for coupling, with at least one group reacting preferably with SH groups. The invention therefore also relates to colloidal metal particles with a coating of non cross-linked SH-aminodextran carrying SH-reactive linker molecules. The present invention particularly includes core-shell particles to which biomolecules are coupled. Here it is not important whether the coupling of the biomolecules is done directly to the SH-functions of the SH-aminodextran or whether homo- or heterobifunctional linkers are used for coupling. The core-shell particles coupled to biomolecules are also called "conjugates".

In a particularly preferable form, binding partners for further biomolecules, particularly antibodies, are coupled to the colloidal metal particles according to the invention.

Figure 2:
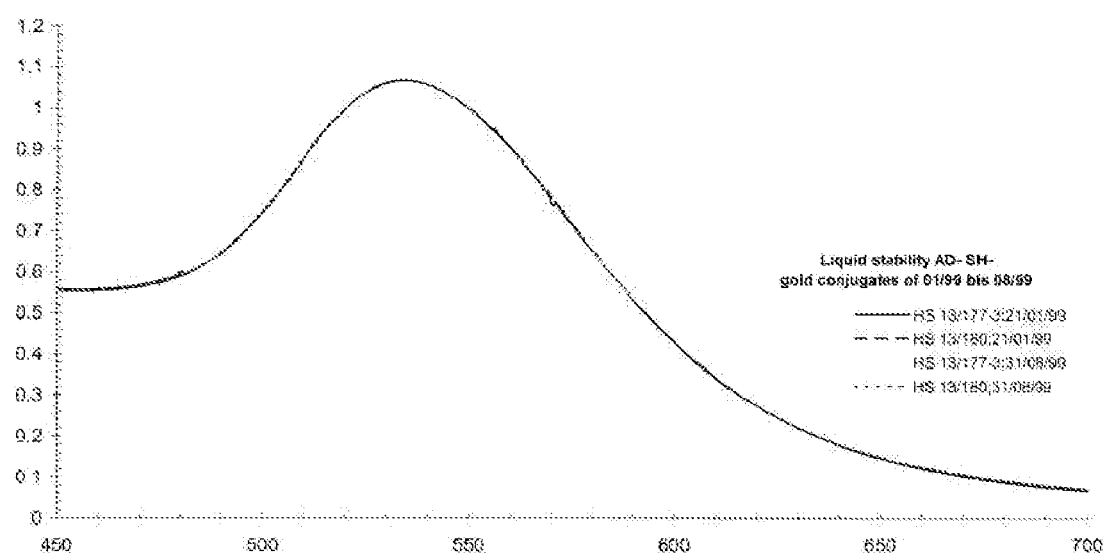
FIG. 2: UV/Vis analysis of antibody gold conjugates produced using core-shell particles according to the invention The almost identical curve form of both preparations before and after stress in the UV/Vis analysis proves that both batches produced according to the invention show the same behavior under the storage conditions chosen (approximately 7 months at 4° C.), and no changes have occurred. This means that the conjugates are stable under the conditions tested.
Figure 3:
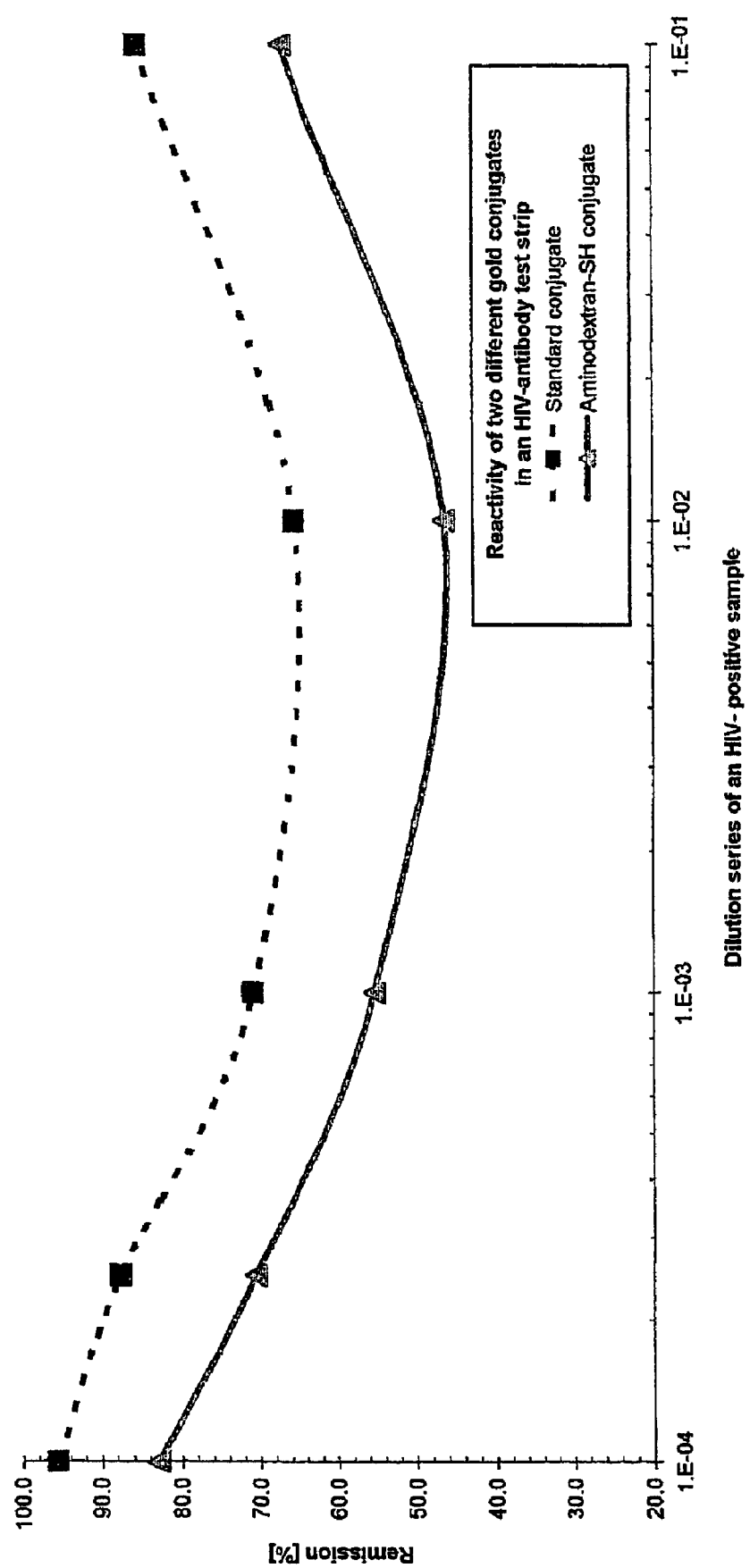
FIG. 3: Remission analysis of a core-shell particle according to the invention and of a particle according to the state of the art A monoclonal antibody (MAB) was bound to colloidal gold particles produced according to the invention. Furthermore, an MAB-gold conjugate was produced according to methods of the state of the art. Both conjugates were evaluated by means of remission analysis. A lower remission value is identical with an improved sensitivity of the conjugate in the test.

It has been shown that antibody conjugates according to the invention, i.e., conjugates of gold-core-shell particles and antibodies according to the invention, are advantageous over analogous state of the art particles. When comparing the storage stability of antibody-gold particle conjugates produced with gold particles according to the state of the are (FIG. 1) or, respectively, using the core-shell particles according to the invention (FIG. 2), it becomes clear that the last-mentioned are much more stable. Besides the surprisingly good stability, the conjugates according to the invention exhibit better behavior in immunological test systems. The results regarding the immunological sensitivity of two different antibody-gold particle conjugates given in FIG. 3 are derived from a so-called quick test of a test-strip format. From FIG. 3, the expert can gather that the test is more sensitive when using the conjugates according to the invention.

Usually, "quick tests" are to be understood as test systems with single or all reactive test components impregnated on one carrier structure, e.g., in the form of a test strip so that for the test procedure itself, it is sufficient to apply a sample fluid. Analyte molecules in the sample react with the impregnated detection reagents while the sample fluid passes the test strip. Generally the test strip includes a provision for a detection zone, e.g., in the form of a line of a tightly bound specific binding partner to gather the analyte-detection reagent complexes. The signal intensity in this detection zone can then be determined with the naked eye or by appropriate analytical instruments. A wide variety of such quick test embodiments are known to the expert, e.g., form EP B 186,799 or EP A 299,428).

The conjugates according to the invention can thus, for example, be used in a quick test for the detection of anti-HIV antibodies.

Quantitative evaluation of test strip results by means of remission measurement via a chromometer showed that conjugates produced according to the invention had significantly higher signals than other comparable test strips with adsorptively loaded conjugates. For comparison, FIG. 3 shows a dilution series of an HIV-positive sample for both conjugates. A lower remission is synonymous with higher sensitivity regarding the concentration series measured. For test strip performance, this is a remarkable advantage.

The use of the conjugates according to the invention comprising biomolecules, in particular antibodies, and colloidal SH-aminodextran-metal particles in test systems as a marker or detection reagent, especially in immunological test procedures and particularly preferably in so-called quick tests, is therefore a further particularly preferable embodiment of the present invention.

The use of the conjugates according to the invention is possible in all usual immunological test procedures known to the expert. In all known immunoassays, the analyte is specifically detected directly or indirectly in a sample by means of binding in one or several immunological binding partners.

The usual test formats, for example, heterogeneous or homogeneous test procedures, are known to the expert and need no further explanation here.

A further subject matter of the invention, therefore, is a procedure, in particular an immunological procedure, for the detection of an analyte in a sample where the conjugates of core-shell particles according to the invention are used together with biomolecules as a marker or detection reagent.

SPECIFIC EMBODIMENTS

Example 1

Insertion of SH Groups in Aminodextran 5 g of aminodextran with a molecular weight of approximately 40,000 and a concentration of approximately 30 amino groups per molecule were dissolved in 200 ml of phosphate buffer, pH 8.5. 1.225 g SATP were dissolved in 62 ml DMSO and added to the aminodextran solution. The mixture was stirred at room temperature for 3 hours and then dialyzed. The release of the SH groups was achieved by adding 694 mg of hydroxylamine dissolved in 2 ml water. The pH was adjusted to 6.0 and after one hour dialyzed against phosphate buffer, pH 6.0.

Example 2

Coating of Colloidal Gold With SH-Modified Aminodextran 400 ml of a gold sol produced according to the state of the art with a concentration of 400 OD (optical density units) was adjusted to a pH of 5.6. Subsequently, 400 μg of the SH-aminodextran produced according to Example 1 was added to 10 mM K acetate, pH 5.6, and stirred for 2 hours.

Example 3

Insertion of Maleimide Groups (MH) Into the Antibody 18 mg immunoglobulin of a monoclonal murine antibody against digoxigenin (MAB<Dig>M-IgG) were dissolved in 1 ml phosphate buffer, pH 7. 6.9 mg of maleinimidohexyl-N-hydroxysuccinimide (MHS) were dissolved in 690 μl DMSO. 330 μl of the antibody solution were subsequently mixed with 10 μl of the MHS solution and stirred at 4° C. for 2 hours. Afterwards dialysis was performed overnight.

Example 4

Production of the Conjugates From MH-IgG and SH-Aminodextran Gold

360 OD of the SH-aminodextran gold were adjusted to pH 6.6. Subsequently 720 μg of the MH-modified antibody, dissolved in 40 ml acetate/TRIS buffer pH 6.6 were added, the pH adjusted to 7.0, and the mixture stirred at 4° C. overnight. The surplus SH and maleimide groups which had not completely reacted were then stopped by adding thioglucose and iodo-acetamide. Subsequently, 400 mg of bovine serum albumin were added and the pH adjusted to 7.8.

Example 5

Production of an Adsorptively Loaded Conjugate

The solution of the antibody to be loaded was dialysed against the appropriate loading buffer, TRIS, pH 8.0. Possibly existing aggregates were removed by filtration. The pH value of the gold sol solution was adjusted to the pH of the protein solution. The antibody solution (10 μg protein/OD gold) was added to the gold sol solution and incubated for 2 hours. Subsequently it was saturated by adding a 10% BSA solution (final concentration approximately 1% BSA). Purification of the conjugate was reached by dialysis.

Example 6

Function Evaluation for the conjugates According to the Invention

Liquid Stability

MAB<Dig>M-IgG-aminodextran-SH conjugates as well as conjugates from MAB<Dig>M-IgG and gold sol particles from the state of the art were stored at 4° C. for 7 months. Over the period observed, the conjugates according to the invention remained unchanged with regard to their UV/Vis spectrum. Adsorptively loaded conjugates exhibited, however, a changed spectrum in accordance with a broader particle size of distribution (cf. FIGS. 1 and 2).

Functionality Test

The described MAB<Dig>M-IgG-aminodextran-SH conjugates were evaluated in an anti-HIV antibody test and compared with an adsorption loaded conjugate.

The test format was designed as a dry test with test strips having the HIV-specific reaction partners (dioxigenylated) dried on one carrier fleece. The MAB<Dig>M-IgG-gold conjugate was dried on a separate carrier fleece.

By application of the serum sample, the dried reagents and reaction partners were re-solubilized, reacted with the HIV-specific antibodies to be detected from the sample, and were indicated in a separate detection field by the red colour of the gold conjugate.

What is claimed is:

1. An immunological test method for determining the amount or presence of an analyte in a sample comprising combining the sample with a detection reagent comprising a specific binding partner for the analyte and a core-shell particle, wherein the core comprises a colloidal metal particle and the shell comprises non cross-linked dextran or non cross-linked aminodextran wherein said dextran or aminodextran is modified to carry SH groups to which the specific binding partner for the analyte is bound directly or via a linker, whereby the analyte in the sample binds to the detection reagent to form a complex, and determining the amount of binding of the analyte by the detection reagent by measuring signal intensity from the complex formed as a measure of the amount or presence of the analyte in the sample.

2. The method of claim 1 wherein the test method uses a test strip format.

3. A method for producing a detection reagent for use in an immunological test procedure to determine an analyte in a sample, the method comprising modifying dextran or aminodextran by inserting SH groups,
coating colloidal gold particles with the SH-modified dextran or aminodextran,
modifying an antibody immunologically reactive with the analyte by inserting maleimide groups, whereby the maleimide groups are reactive with the SH groups, and
combine the coated particles with the modified antibody such that the particles and antibody bind via the SH and maleimide groups, thereby forming the detection reagent.

* * * * *